United States Patent
Kamegawa et al.

(10) Patent No.: US 7,477,723 B2
(45) Date of Patent: Jan. 13, 2009

(54) X-RAY FLUOROSCOPE

(75) Inventors: Masayuki Kamegawa, Kyoto (JP); Yoshio Kuni, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 11/663,502

(22) PCT Filed: Sep. 2, 2005

(86) PCT No.: PCT/JP2005/016115

§ 371 (c)(1),
(2), (4) Date: Mar. 22, 2007

(87) PCT Pub. No.: WO2006/033225

PCT Pub. Date: Mar. 30, 2006

(65) Prior Publication Data

US 2007/0286341 A1    Dec. 13, 2007

(30) Foreign Application Priority Data

Sep. 22, 2004   (JP) .............................. 2004-275240

(51) Int. Cl.
*G03C 9/00* (2006.01)
*G01N 23/04* (2006.01)

(52) U.S. Cl. .......................... 378/42; 378/63

(58) Field of Classification Search .................... 378/42, 378/44, 45, 46, 57, 62, 63, 206, 207, 208
See application file for complete search history.

(56) References Cited

U.S. PATENT DOCUMENTS

| 4,246,607 | A | * | 1/1981 | Vijverberg ................ 378/98.5 |
| 5,605,531 | A | * | 2/1997 | Lane et al. .................. 600/118 |
| 2002/0012450 | A1 | * | 1/2002 | Tsujii ........................ 382/103 |

FOREIGN PATENT DOCUMENTS

| JP | 04-158208 A | 6/1992 |
| JP | 06-317542 A | 11/1994 |
| JP | 11-118736 A | 4/1999 |
| JP | 3203766 B | 6/2001 |
| JP | 2003-202304 A | 7/2003 |
| JP | 2003-279502 A | 10/2003 |

* cited by examiner

*Primary Examiner*—Irakli Kiknadze
(74) *Attorney, Agent, or Firm*—Sughrue Mion, PLLC

(57) ABSTRACT

An optical camera 5 for photographing a fluoroscopy object W on a sample stage 3 is provided. Prior to a fluoroscopic operation, the sample stage 3 is driven, and the fluoroscopy object W is photographed in a plurality of postures by the optical camera 5, and optical images are stored in a storage device 14. Among the optical images stored in the storage device 14, an optical image O that is closest to an image of the fluoroscopy object W viewed from the fluoroscopy direction at current time is selected and displayed on a display 13 during the fluoroscopic operation. This enables intuitive grasping of the fluoroscopy direction, and intuitive grasping of the fluoroscopy position is also enabled by superimposing and displaying a marker M, which represents a position of an X-ray optical axis L, in addition to the optical image O.

13 Claims, 3 Drawing Sheets

X-RAY FLUOROSCOPE

TECHNICAL FIELD

Figure 1:
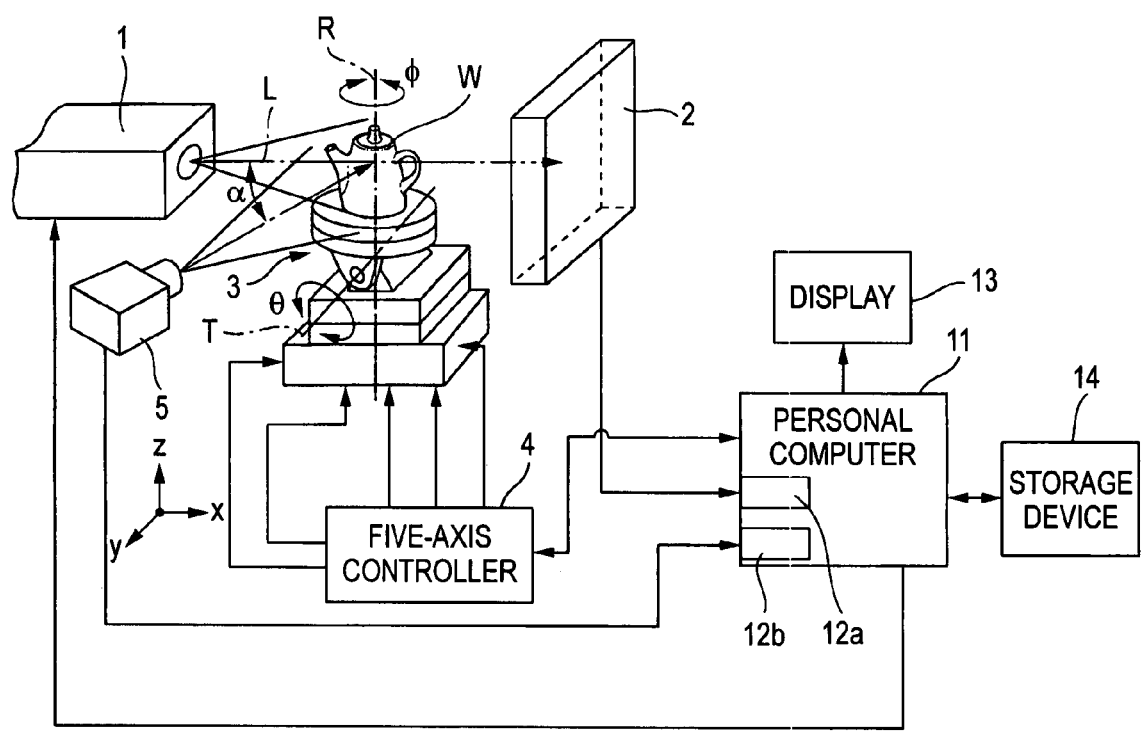

The present invention relates to an industrial X-ray fluoroscope, and more particularly, to an X-ray fluoroscope suitable for nondestructively observing internal defects of objects such as aluminum castings.

BACKGROUND ART

An X-ray fluoroscope in which an sample stage for moving and rotating while fixing an object to be inspected (a fluoroscopy object) is interposed between an X-ray source and an X-ray detector has hitherto been known as an apparatus for nondestructively inspecting internal defects of an object such as an aluminum casting (e.g., see Patent Document 1).

In an apparatus of this type, as for the position and posture of the fluoroscopy object based on the position and rotational angle of the sample stage, an operator usually operates a driving mechanism of the sample stage while viewing an X-ray fluoroscopic image or checking the actual position and posture of the fluoroscopy object through an observation window provided to a cover of the apparatus or the like.

Patent Document 1: JP-A-2003-279502

DISCLOSURE OF THE INVENTION

Problem to be Solved by the Invention

Incidentally, in the X-ray fluoroscope as mentioned above, for instance, in a case where fluoroscopic operation is performed under high magnification, when from which direction the fluoroscopy object is viewed fluoroscopically and which position is viewed fluoroscopically are uncertain, there are usually performed operating procedures such as decreasing fluoroscopic magnification by changing the distance between the X-ray source and the fluoroscopy object, checking a fluoroscopy direction and the center position of a view field by using, for example, an entire fluoroscopic image of the fluoroscopy object, and performing fluoroscopic operation by increasing the fluoroscopic magnification again. This practice contributes to a decrease in working efficiency.

The present invention has been conceived in the light of such circumstances, and provides an X-ray fluoroscope which enables intuitive and easy grasping of a fluoroscopy position as well as a fluoroscopy direction of an fluoroscopy object without performing operations such as checking a fluoroscopy position and a fluoroscopy direction by reducing magnification.

Means for Solving a Problem

In order to solve the problem, an X-ray fluoroscope of the present invention comprises:

an X-ray source and an X-ray detector which are arranged to be opposed to each other;

a sample stage for fixing a fluoroscopy object, being provided between the X-ray source and the X-ray detector;

a driving mechanism for moving and rotating the sample stage relatively with respect to a pair of the X-ray source and the X-ray detector;

an optical camera for photographing the fluoroscopy object on the sample stage;

a storage section for storing a plurality of optical images of the fluoroscopy object being photographed in advance by the optical camera from a plurality of directions by driving the sample stage; and an optical image display section for, at the time of observation of an X-ray fluoroscopic image, selecting an optical image that is closest to a state of the fluoroscopy object being viewed from an X-ray fluoroscopy direction, from the plurality of optical images stored in the storage section, on the basis of a position and a rotating state of the sample stage, and displaying the selected optical image on a display.

Here, in the present invention, there can be preferably adopted a configuration wherein the optical image display section displays a marker representing at least one of a position and a direction of an X-ray optical axis on a screen of the display by superimposing the marker on the optical image of the fluoroscopy object.

In the present invention, there can be adopted a configuration wherein the optical image display section displays an optical image that is photographed from a direction perpendicular to the X-ray fluoroscopy direction concurrently or in a switchable manner on the display, in addition to the optical image that is closest to the state of the fluoroscopy object being viewed from the X-ray fluoroscopy direction.

Moreover, in the present invention, there can also be adopted a configuration further comprising a controller for automatically driving the driving mechanism so that, by moving the marker representing at least one of the position and the direction of the X-ray optical axis on the display, a relationship between the X-ray optical axis and the fluoroscopy object coincides with at least one of a position and a direction of the moved marker.

According to the configuration of the X-fluoroscope, an optical (external appearance) image of the fluoroscopy object is photographed in advance from a plurality of directions before fluoroscopic (inspecting) operation by an optical camera provided in the system, and the image is stored previously. In accordance with the position and posture of the sample stage during the fluoroscopic operation, an optical image that is closest to the state of the fluoroscopy object being viewed from the X-ray fluoroscopy direction at that point in time is displayed on a display. As a result of this, the operator can ascertain the image of the fluoroscopy object viewed from the X-ray fluoroscopy direction at all times during the fluoroscopic operation, and intuitively determine from which direction the fluoroscopy object is fluoroscopically viewed.

When, in addition to having the above-described configuration, the X-ray fluoroscope has a function of superimposing and displaying a marker which represents the position and/or direction of an X-ray optical axis on an optical image displayed on the display, the center of the field of view as well as the fluoroscopy direction of the fluoroscopy object can be intuitively grasped.

Moreover, in the X-ray fluoroscope, when an optical image photographed from a direction perpendicular to the above-described optical image can be displayed concurrently or in a switchable manner in addition to the above-described optical image, the fluoroscopy direction of an fluoroscopy object whose front and back are difficult to distinguish from each other can be readily determined. Moreover, as a result of a combination of the X-ray fluoroscope with the marker display, displaying the direction of the X-ray optical axis becomes easy.

According to the X-ray fluoroscope, the sample stage is configured so as to be automatically driven so that, by moving the marker displayed with the optical image, a positional and/or directional relationship between the fluoroscopy object and the X-ray optical axis coincides with the positions and/or directions of the marker and fluoroscopy object after the movement. Thus, change of the fluoroscopy direction and position can also be performed intuitively.

ADVANTAGES OF THE INVENTION

According to the present invention, since an optical image of a fluoroscopy object viewed from the X-ray fluoroscopy direction is displayed on a display, an operator can intuitively grasp from which direction the fluoroscopy object is viewed fluoroscopically at all times without checking the fluoroscopy direction and position by decreasing the fluoroscopic magnification as in the related art.

Further, when the X-ray fluoroscopy is configured in such a way that a marker representing the position and/or direction of the X-ray optical axis is displayed as being superimposed on an optical image viewed from the X-ray fluoroscopy direction, the center of a fluoroscopic view field as well as the fluoroscopy direction can be grasped intuitively.

As in the case of the X-ray fluoroscope, when, in addition to the optical image viewed from the X-ray fluoroscopy direction, the optical image photographed from a direction perpendicular to that optical image are displayed concurrently or in a switchable manner, the X-ray fluoroscopy direction can be grasped in a more reliable manner. Display of the marker in the X-ray fluoroscope also becomes easy.

As in the case of the above-described X-ray fluoroscope, when the sample stage is configured so as to be automatically driven and controlled so that, by moving the marker on the optical image, a relationship between an actual fluoroscopy object and the X-ray optical axis coincides with a relationship between the marker and the optical image after the movement, change of the fluoroscopy direction and/or fluoroscopy position of the fluoroscopy object can also be performed intuitively.

BRIEF DESCRIPTIONS OF THE DRAWINGS

FIG. 1 A block diagram of an embodiment of the present invention; that is, a view showing in combination a schematic diagram showing a mechanical configuration and a block diagram showing a system configuration.

Figure 2:
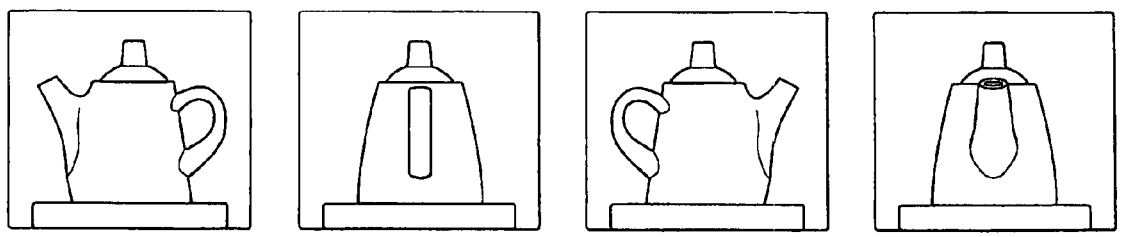
Figure 2:
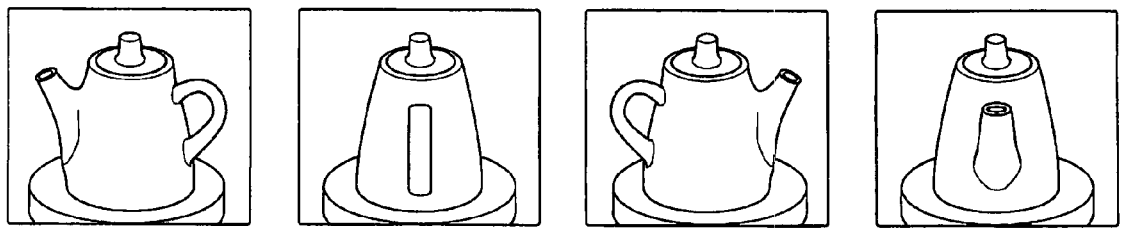

FIG. 2 A view showing an example of an optical image obtained by photographing an external appearance of a fluoroscopy object W by using a CCD camera 5 according to an embodiment of the present invention.

Figure 3:
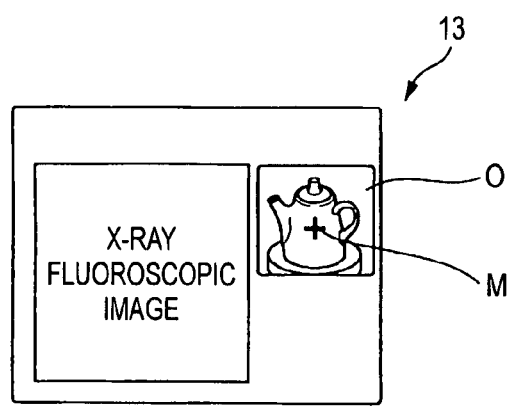

FIG. 3 A descriptive view of an example display of a display 13 according to an embodiment of the present invention.

Figure 4:
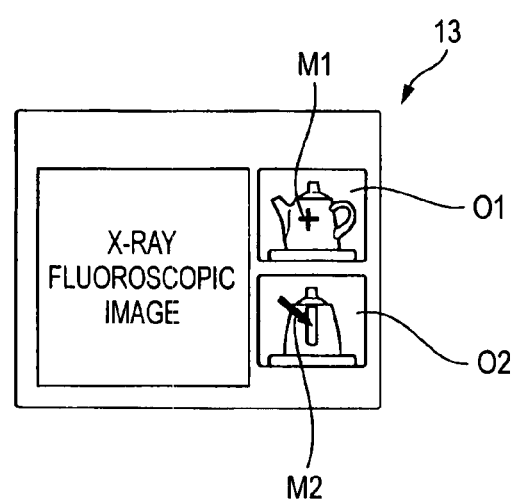

FIG. 4 A descriptive view of an example display of the display according to another embodiment of the present invention.

Figure 5:
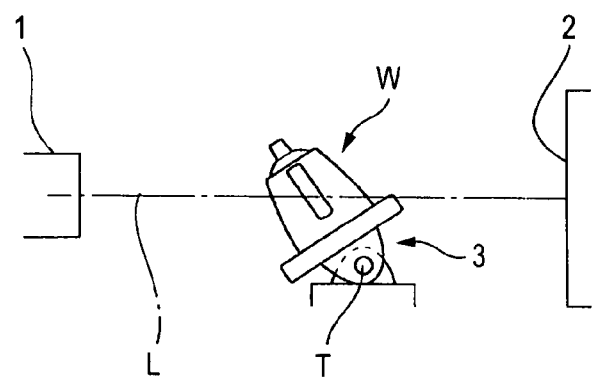

FIG. 5 A view showing a relationship between a fluoroscopy object W and an X-ray optical axis L in a displayed state of FIG. 4.

DESCRIPTIONS OF THE REFERENCE NUMERALS

1 X-RAY SOURCE
2 X-RAY DETECTOR
3 SAMPLE STAGE
4 FIVE-AXIS CONTROLLER
5 CCD CAMERA
11 PERSONAL COMPUTER
12a, 12b CAPTURE BOARD
13 DISPLAY
14 STORAGE DEVICE
R ROTATIONAL CENTER AXIS
T CENTER AXIS OF TILTING
W FLUOROSCOPIY OBJECT

BEST MODE FOR IMPLEMENTING THE INVENTION

An embodiment of the present invention will be described hereinbelow by reference to the drawings.

FIG. 1 is a block diagram of an embodiment of the present invention; that is, a view showing in combination a schematic diagram showing a mechanical configuration and a block diagram showing a system configuration.

An X-ray detector 2 is arranged by horizontally being opposed to an X-ray source 1, and a sample stage 3 for mounting a fluoroscopy object W is interposed therebetween. The sample stage 3 incorporates a moving mechanism to move in a direction of the X-ray optical axis (in the direction of an x-axis) from the X-ray source 1, the direction of a y-axis perpendicular to the direction of the x-axis on a horizontal plane, and the direction of a vertical z-axis. Further, the sample stage also incorporates a rotating mechanism for rotation ($\phi$) around the rotational center axis R that is parallel to the z-axis and a tilting mechanism for tilting ($\theta$) around the center axis T of tilting that is parallel to the y-axis. These mechanisms are driven and controlled by a drive signal from a five-axis controller 4 that is under the control of a personal computer The X-ray detector 2 is a combination of an image intensifier with a CCD or a panel-type detector. An output from the X-ray detector 2 is captured by a capture board 12a incorporated in the personal computer 11 and displayed in a live manner as an X-ray fluoroscopic image on a display 13.

A CCD camera 5 is disposed adjacent to the X-ray source 1. An optical axis of the CCD camera 5 is set on the same horizontal plane as an X-ray optical axis L from the X-ray source 1, and also set at a position shifted from the X-ray optical axis L for a known angle $\alpha$ on that plane. This CCD camera 5 is for photographing the fluoroscopy object W on the sample stage 3 from a plurality of directions prior to X-ray fluoroscopy operation, as will be described below. An output from the CCD camera 5 is captured by another capture board 12b incorporated in the personal computer 11, and optical images (external appearance images) of the fluoroscopy object W photographed from the respective directions are stored in a storage device 14.

An operating method for and operation of the embodiment of the present invention configured as mentioned above will now be described. After the fluoroscopy object W is put on the sample stage 3, prior to the X-ray fluoroscopy, the sample stage 3 is driven and external appearance images of a plurality of postures are photographed by the CCD camera 5 while changing the posture of the fluoroscopy object W consecutively, as illustrated in FIG. 2. This photographing operation is automatically performed by issuing a command to the personal computer 11. Specifically, for instance, the external appearance of the fluoroscopy object W is photographed by rotating the sample stage 3 around the rotational axis R for 360° in increments of, e.g., several degrees to tens of degrees, in a state that the sample stage positions at its original position. Moreover, the external appearance of the fluoroscopy object W is photographed by tilting the sample stage around an axis T of tilting ($\theta$) in several steps in increments of several degrees at each angle of rotation $\phi$. The thus-photographed images are stored in the storage device 14. There is a possibility that an optical image becomes excessively large or small depending on the size of the fluoroscopy object W. This problem can be handled by providing a zoom function to the CCD camera 5 or a digital zoom function to the personal computer 11.

After photographing of the external appearance images is completed, X-ray fluoroscopy is performed. At this time, as illustrated in FIG. 3, an optical image O closest to the fluoroscopy object W that is viewed from the X-ray fluoroscopy direction is selected among optical images (external appearance images) of the fluoroscopy object W stored in the storage device 14, and displayed on the display 13 along with an X-ray fluoroscopic image of the fluoroscopy object W. This selecting operation is performed by using, as a rotational angle $\phi$ of the sample stage 3, a rotational angle obtained by correcting the rotational angle $\phi$ at this point of time for an angle ($\pi$-$\alpha$) on the side of the X-ray detector 2 of the optical axis of the CCD camera 5 with respect to the X-ray optical axis L; and by selecting an optical image photographed at the same tilting angle as the tilting angle $\theta$ of the sample stage 3 at this point of time.

A marker M is superimposed on such an optical image O, and the position of the X-ray optical axis L is displayed by the marker M. This marker M is made to position in the center of the screen of the optical image O at all times. When the sample table 3 is moved from the original position in the direction of the y-axis and the direction of the z-axis, the optical image O of the fluoroscopy object W is moved on the screen by a corresponding dimension through scrolling. Alternatively, the position of the marker M may also be moved with the optical image O being fixed. When the fluoroscopic enlarging magnification is changed by moving the sample stage 3 in the direction of the x-axis, the optical image and the marker M are not moved.

By a display of such an optical image mentioned above, even when the operator is fluoroscopically viewing the fluoroscopy object W at high fluoroscopic magnification by causing the sample stage 3 to approach to the side of the X-ray source 1 in the direction of the x-axis, the operator can intuitively grasp which portion of the fluoroscopy object W is fluoroscopically viewed as the center of a view field.

In the above embodiment, photographing is carried out while two parameters $\phi$ and $\theta$ are varied in a plurality of situations respectively to thereby obtain optical images to be previously stored in a storage device. However, for instance, when the optical images are photographed while $\phi$ is changed at intervals of 5°, 72 images are necessary at minimum, and when the optical images are photographed while changing $\theta$ at each of the angles of $\phi$, the number of required optical images O becomes enormous. To avoid this problem, only $\phi$ may be used as a parameter, and $\theta$ can be dealt with by way of displaying the marker.

An example of the display is provided below. FIG. 4 is a descriptive view of the example display. As shown in FIG. 5, this display corresponds to a state where the fluoroscopy object W is tilted by $\theta$. Specifically, in this example, an optical image O1 viewed from the X-ray fluoroscopy direction similarly as the above-described example and an optical image O2 photographed from a direction perpendicular to the X-ray fluoroscopy direction are displayed as optical images. Markers M1, M2 representing the X-ray optical axis are displayed while being superimposed on the respective optical images O1, O2. The marker M1 to be superimposed on the optical image O1 is taken as a point representing a position of the X-ray optical axis L, as in the case of the previous example. The marker M2 to be superimposed on the optical image O2 is taken as a line imparted with an angle corresponding to the tilting angle of $\theta$ shown in FIG. 5. As a result, when the sample stage 3 is tilted by $\theta$, the operator can be informed that the fluoroscopy direction is tilted by $\theta$ by the posture of the marker M2, without displaying the optical image corresponding to the tilting angle.

When the marker M or the markers M1 and M2 such as those mentioned above are moved on the optical image O or the optical images O1 and O2 by use of a mouse or the like, the personal computer 11 issues a control command to the five-axis controller 4 thereby enabling automatic movement of the sample stage 3, so that a relationship between an actual fluoroscopy object W and the X-ray optical axis L coincides with a relationship between the optical image and the marker after the movement. Specifically, when the marker M or M1 is moved on the screen in the direction of "y" and the direction of "z," the optical image O or the optical images O1 and O2 are scrolled by following that and the marker M or M1 returns to the center of the screen. Concurrently, the sample stage 3 moves in the direction of "y" and the direction of "z" for an amount corresponding to the amount of scroll. When the angle of the marker M2 is changed, the sample stage 3 is tilted for an angle corresponding to the amount of change. By imparting such a function, the operator can intuitively change the fluoroscopy direction and the fluoroscopy position while viewing a screen of the optical image.

FIG. 4 shows the example where the optical images O1, O2 perpendicular to each other are displayed simultaneously. However, when restrictions are imposed on a display area, there may also be adopted a configuration where these optical images O1, O2 are displayed in a selectively-switchable manner.

The above embodiment has provided the example where the sample stage 3 is provided with the tilting mechanism. However, the tilting operation can also be implemented by holding the X-ray source 1 and the X-ray detector 2 integrally by a C-shaped frame or the like, and tilting the pair with respect to the sample stage 3. In this case, the CCD camera 5 may also be tilted with respect to the sample stage 3. The CCD camera 5 and the X-ray source 1 may also be held integrally by a frame or the like. Although the present invention has been described in detail by reference to the specific embodiments, it is apparent to persons skilled in the art that various alterations or modifications can be added without departing from the spirit and scope of the present invention.

The present invention is based on Japanese Patent Application (No. 2004-275240) filed on Sep. 22, 2004, the contents of which are incorporated herein by reference.

The invention claimed is:
1. An X-ray fluoroscope, comprising:
an X-ray source and an X-ray detector which are arranged to be opposed to each other;
a sample stage for fixing a fluoroscopy object, being provided between the X-ray source and the X-ray detector;
a driving mechanism for moving and rotating the sample stage relatively with respect to a pair of the X-ray source and the X-ray detector;
an optical camera for photographing the fluoroscopy object on the sample stage;
a storage section for storing a plurality of optical images of the fluoroscopy object being photographed in advance by the optical camera from a plurality of directions by driving the sample stage; and
an optical image display section for, at the time of observation of an X-ray fluoroscopic image, selecting an optical image that is closest to a state of the fluoroscopy object being viewed from an X-ray fluoroscopy direction, from the plurality of optical images stored in the storage section, on the basis of a position and a rotating state of the sample stage, and displaying the selected optical image on a display.

2. The X-ray fluoroscope according to claim 1, wherein the optical image display section displays a marker representing at least one of a position and a direction of an X-ray optical axis on a screen of the display by superimposing the marker on the optical image of the fluoroscopy object.

3. The X-ray fluoroscope according to claim 2, further comprising:
   a controller for automatically driving the driving mechanism so that, by moving the marker representing at least one of the position and the direction of the X-ray optical axis on the display, a relationship between the X-ray optical axis and the fluoroscopy object coincides with at least one of a position and a direction of the moved marker.

4. The X-ray fluoroscope according to claim 2, wherein the optical image display section displays an optical image that is photographed from a direction perpendicular to the X-ray fluoroscopy direction concurrently or in a switchable manner on the display, in addition to the optical image that is closest to the state of the fluoroscopy object being viewed from the X-ray fluoroscopy direction.

5. The X-ray fluoroscope according to claim 4, further comprising:
   a controller for automatically driving the driving mechanism so that, by moving the marker representing at least one of the position and the direction of the X-ray optical axis on the display, a relationship between the X-ray optical axis and the fluoroscopy object coincides with at least one of a position and a direction of the moved marker.

6. The X-ray fluoroscope according to claim 1,
   wherein the optical image display section displays an optical image that is photographed from a direction perpendicular to the X-ray fluoroscopy direction concurrently or in a switchable manner on the display, in addition to the optical image that is closest to the state of the fluoroscopy object being viewed from the X-ray fluoroscopy direction.

7. The X-ray fluoroscope according to claim 6, further comprising:
   a controller for automatically driving the driving mechanism so that, by moving the marker representing at least one of the position and the direction of the X-ray optical axis on the display, a relationship between the X-ray optical axis and the fluoroscopy object coincides with at least one of a position and a direction of the moved marker.

8. The X-ray fluoroscope according to claim 1, wherein the selected optical image and the X-ray fluoroscopic image are concurrently displayed on the display.

9. An X-ray fluoroscopic method in an X-ray fluoroscope having an X-ray source and an X-ray detector which are arranged to be opposed to each other, and a sample stage for fixing a fluoroscopy object, being provided between the X-ray source and the X-ray detector, the X-ray fluoroscopic method comprising:
   storing a plurality of optical images being obtained in advance by photographing the fluoroscopy object by the optical camera from a plurality of directions while driving the sample stage by moving and rotating the sample stage relatively with respect to a pair of the X-ray source and the X-ray detector; and
   at the time of observation of an X-ray fluoroscopic image, selecting an optical image that is closest to a state of the fluoroscopy object being viewed from an X-ray fluoroscopy direction, from the plurality of stored optical images, on the basis of a position and a rotating state of the sample stage, and displaying the selected optical image on a display.

10. The X-ray fluoroscopic method according to claim 9, wherein the selected optical image and the X-ray fluoroscopic image are concurrently displayed on the display.

11. The X-ray fluoroscopic method according to claim 9, further comprising displaying a marker representing at least one of a position and a direction of an X-ray optical axis on a screen of the display by superimposing the marker on the optical image of the fluoroscopy object.

12. The X-ray fluoroscopic method to claim 11, further comprising moving the marker representing at least one of the position and the direction of the X-ray optical axis on the display, a relationship between the X-ray optical axis and the fluoroscopy object coincides with at least one of a position and a direction of the moved marker.

13. X-ray fluoroscopic method according to claim 9, wherein an optical image that is photographed from a direction perpendicular to the X-ray fluoroscopy direction is displayed concurrently or in a switchable manner on the display, in addition to the optical image that is closest to the state of the fluoroscopy object being viewed from the X-ray fluoroscopy direction.

* * * * *